United States Patent [19]
Foley et al.

[11] Patent Number: 5,681,311
[45] Date of Patent: Oct. 28, 1997

[54] OSTEOSYNTHESIS APPARATUS

[75] Inventors: Kevin T. Foley, Memphis, Tenn.; Peter M. Klara, Norfolk, Va.; Keith Maxwell, Asheville, N.C.; Lance Middleton; Matthew M. Morrison, both of Memphis, Tenn.

[73] Assignee: Smith & Nephew, Inc., Memphis, Tenn.

[21] Appl. No.: 575,601

[22] Filed: Dec. 20, 1995

Related U.S. Application Data

[63] Continuation-in-part of Ser. No. 306,670, Sep. 15, 1994, abandoned.

[51] Int. Cl.$^6$ ..................................................... A61B 17/70
[52] U.S. Cl. .............................. 606/61; 606/69; 606/73
[58] Field of Search ............................... 606/61, 69, 70, 606/71, 72, 73

[56] References Cited

U.S. PATENT DOCUMENTS

| | | | |
|---|---|---|---|
| 4,484,570 | 11/1984 | Sutter et al. | 606/72 |
| 4,503,848 | 3/1985 | Caspar et al. | 606/69 |
| 5,085,660 | 2/1992 | Lin | 606/73 |
| 5,261,910 | 11/1993 | Warden et al. | 606/61 |
| 5,324,290 | 6/1994 | Zdeblick et al. | 606/61 |
| 5,344,421 | 9/1994 | Crook | 606/61 |
| 5,364,399 | 11/1994 | Lowery et al. | 606/69 |

FOREIGN PATENT DOCUMENTS

| | | | |
|---|---|---|---|
| 1514-357-A | 10/1989 | U.S.S.R. | |
| WO 88/03781 | 6/1988 | WIPO | 606/70 |

OTHER PUBLICATIONS

McGraw-Hill Encyclopedia of Science & Technology, 7th Edition, Copyright 1992, pp. 315–316 1992.

*Primary Examiner*—Michael Buiz
*Assistant Examiner*—David O. Reip
*Attorney, Agent, or Firm*—Pravel, Hewitt, Kimball & Krieger

[57] ABSTRACT

A bone fixation apparatus having an elongated plate member with at least two pairs of circular openings and a series of openings positioned along the longitudinal plane of the plate member with the circular openings and the series of openings each having a central vertical axis. The circular openings and series of openings each form a cavity with walls extending between the upper and lower plate member surfaces with at least a plurality of the cavities having smaller diameter portions at the plate member upper and lower surfaces and a larger diameter portion therebetween. The cavities are configured in the shape of two inverted cones with matching base circles for allowing transverse and longitudinal angulation of an implanted bone screw. A plurality of bone screws each have a threaded first end portion adapted for implantation into a patient's bone mass and a generally ellipsoid shaped enlarged second end portion. A locking member connects to the second end portion of each bone screw for expanding the second end portion so as to grip the cavity wall of the plate member and for locking each bone screw into a selected position within the circular openings and series of openings of the plate member.

37 Claims, 4 Drawing Sheets

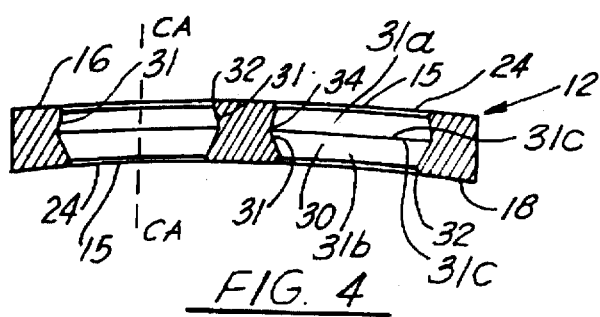
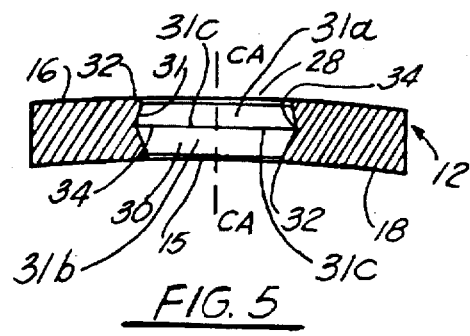
FIG. 4    FIG. 5
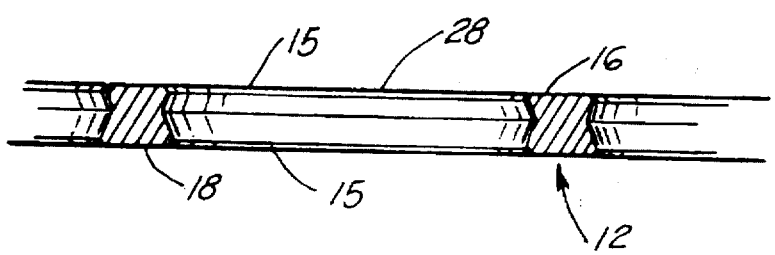
FIG. 6
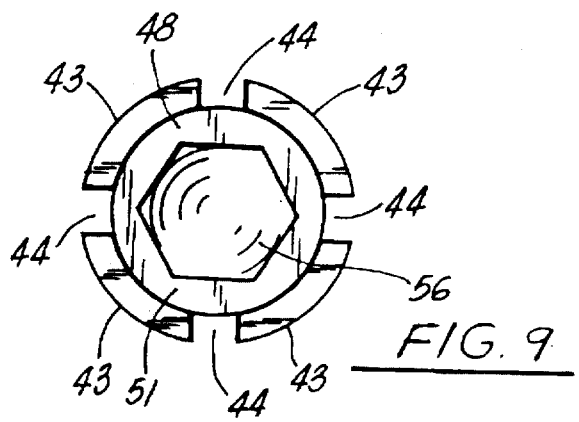
FIG. 9
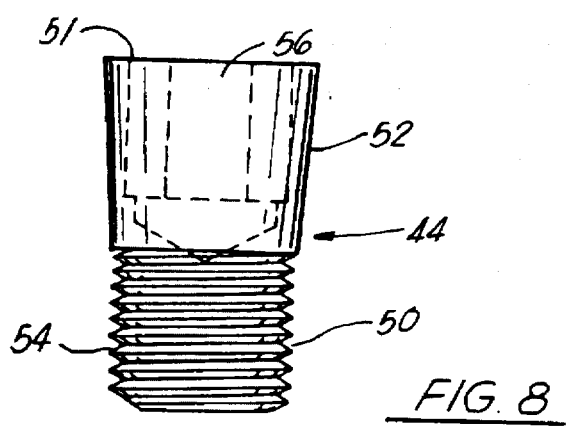
FIG. 8
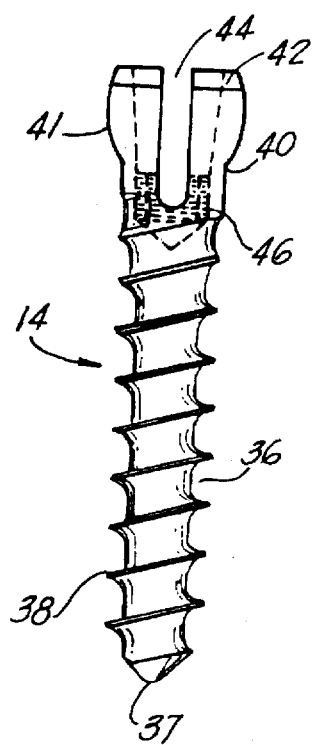
FIG. 7

5,681,311

1

OSTEOSYNTHESIS APPARATUS

SPECIFICATION

This application is a continuation-in-part application of application Ser. No. 306,670 filed Sep. 15, 1994 now abandoned.

FIELD OF THE INVENTION

The present invention relates to an improved bone or spinal fixation apparatus in the form of an elongated plate member and a locking bone screw. The apparatus has particular utility in anterior cervical spine fixation by providing a plate that allows for angulation of the bone screws and a locking bone screw that secures the bone screws into the plate member at a selected angle corresponding to a thick region of the bone mass.

BACKGROUND OF THE INVENTION

There are a number of surgical procedures which require fixation of portions of the spine with respect to one another. Typically, bone screws are employed in the fixation of the spine where the implantation of the bone screws is a surgical procedure in which one or more surgical openings are formed in adjacent portions of the spine and threaded bone screws are implanted into the surgical openings. Connective structures such as rods or plates extend between the various spine members and are connected to the spine members by the implanted bone screws.

In the treatment of spinal disorders and spinal fractures, both a posterior and an anterior approach is used. The use of plating systems for posterior internal fixation of the spine is well known. Additionally, several plating systems have been developed for anterior internal fixation of the spine. For example, the Syracuse I-plate provides a number of differently-sized I-shaped plates which are engaged across the vertebrae. A contoured anterior spinal fixation plate is known which includes a number of screw openings through the contoured plate. The number of openings simply provide different locations for engaging a bone screw to the vertebrae, and does not allow for angulation of the bone screws. A further problem with the application of spinal fixation systems is the placement of such a system in the cervical region of the spine where correct anatomical fit and lack of bone mass presents a problem.

Even with these known posterior and anterior plate fixation systems, there remains a need for a plate and screw system that allows for variation in screw placement along the longitudinal axis of the plate as well as providing for angulation in both the medial-lateral or transverse plane and the cephalad-caudal or longitudinal plane. There is also a need for a fixation system that provides a locking bone screw mechanism for securely fastening the bone screw in a selected angled position within the plate particulaly for locking a bone screw in the center portion of the plate. There is further a need for a fixation plate that is curved to fit the contours of the vertebrae and is also somewhat bendable during implantation but rigid enough to allow fusion to take place after implantation.

SUMMARY OF THE PRESENT INVENTION

It is thus an object of the present invention to provide a bone fixation system that offers a strong and stable construct for maximum fusion augmentation of any bone structure and yet is versatile enough for a variety of bone configurations and is easy to use. The present invention provides an apparatus that can be used on any segment of the spine and in particular can be made small enough for anterior cervical spine applications. The elongated plate includes at least two pairs of circular openings and a series of openings positioned along the longitudinal axis of the plate. The circular openings and series of openings each form a cavity with walls extending between the upper and lower plate surfaces with the cavities having smaller diameter portions at the upper and lower surfaces and a larger diameter portion therebetween. The cavities are configured in the shape of two inverted cones with matching base circles for allowing transverse and longitudinal angulation of an implanted bone screw.

The bone fixation apparatus further includes a plurality of bone screws each having a threaded end for implanting into a patient's bone mass and an ellipsoid shape enlarged second end portion. The second end portion has a locking member for expanding the second end portion so as to grip the cavity wall of the plate and for locking each bone screw into a selected position within the circular openings and series of openings of the plate.

BRIEF DESCRIPTION OF THE DRAWINGS

For a further understanding of the nature and objects of the present invention, reference should be made to the following detailed description taken in conjunction with the accompanying drawings, in which like parts are given like reference numbers, wherein:

FIG. 4 is a sectional view of a portion of the plate shown at lines 4—4 of FIG. 2;

FIG. 5 is a sectional view of a portion of the plate shown at lines 5—5 of FIG. 2;

FIG. 6 is a partial sectional view of the plate shown at lines 6—6 of FIG. 2;

FIG. 7 is a front view of an embodiment of the apparatus of the present invention illustrating a locking bone screw;

FIG. 8 is a from view of an embodiment of the apparatus of the present invention illustrating a locking member that connects to the bone screw of FIG. 7;

FIG. 9 is a top view of the bone screw of FIG. 7 with the locking member of FIG. 8 in its locked position;

DETAILED DESCRIPTION OF THE PREFERRED EMBODIMENTS

Figure 1:
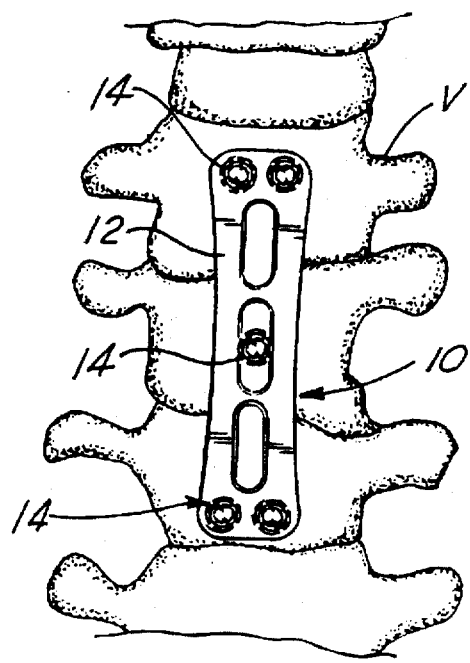
FIG. 1 is an anterior view of an embodiment of the apparatus of the present invention illustrating its placement on the anterior cervical bone tissue.
Figure 2:
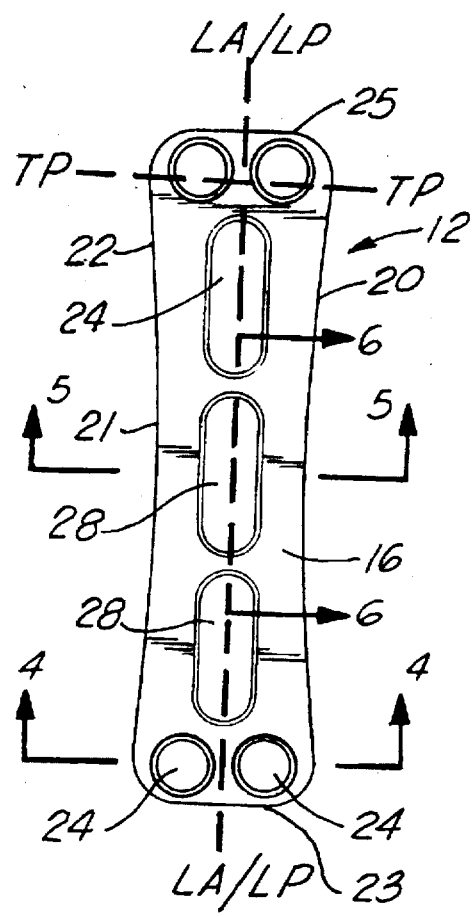
FIG. 2 is a plan view of an embodiment of the apparatus of the present invention illustrating a plate member.
Figure 3A:
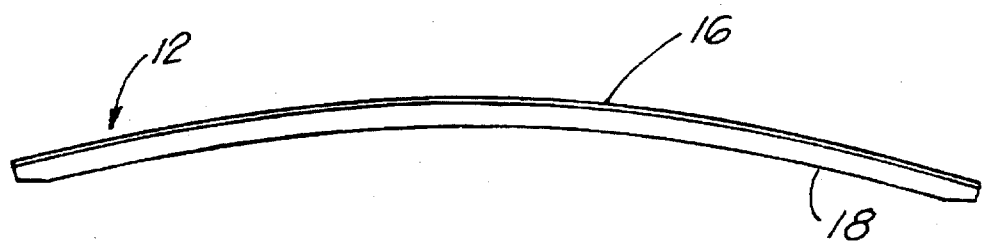
FIG. 3A is a side view of an alternate embodiment of the plate shown in FIG. 2.
Figure 3:
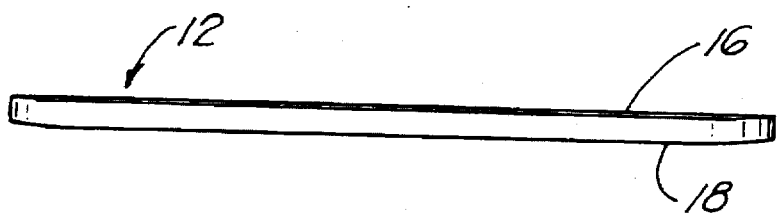
FIG. 3 is a side view of the plate shown in FIG. 2.

FIGS. 1 show the various embodiments of the bone fixation apparatus of the present invention, designated generally by the numeral 10, implanted on the anterior side of cervical vertebrae V of a human patient. The bone fixation apparatus 10 includes a plate member 12 and locking bone screws 14. The plate 12, as shown in FIG. 2, is an elongated plate member 12 having a longitudinal axis LA, a longitudinal plane LP and upper and lower surfaces 16, 18. The plate member 12 has apposed longitudinal side edges 20, 22, first and second ends 23, 25 and a center portion 21. The center portion 21 preferably has a generally smaller width in relation to a larger width at the first and second ends 23, 25. Plate member 12 has a transverse plane TP (FIG. 2) and the plate member 12 can be curved along the transverse plane TP. If curved, the radius of the transverse curve cross-section is between about 22.0 to 77.0 millimeters and is illustrated in FIGS. 4 and 5. As shown in FIG. 3, the plate member 12 can be generally flat along the longitudinal plane LP or the plate member 12 can be curved along the longitudinal plane as illustrated in FIG. 3A. The longitudinal curve can have an arc angle of between about 6° to 40°. The curve in both the transverse plane and the longitudinal plane will allow the plate member 12 to achieve a better fit in on the selective vertebrae particularly in the anterior cervical portion of the spinal column.

The plate member 12 includes a pair of circular openings 24 positioned at its first end 23 and a second pair of circular openings 26 positioned at its second end 25. A series of openings, such as at least one elongated slot 28 is positioned along the longitudinal plane LP of the plate member 12. The series of openings can be positioned along the longitudinal axis LA or offset from the longitudinal axis LA. In one embodiment three elongated slots 28 are positioned along the longitudinal axis LA of the plate member 12. The circular openings 24, 26 and elongated slots 28 have a central vertical axis CA, as illustrated in FIGS. 4 and 5. In an alternate embodiment, more than two pairs of circular openings can be placed on the ends of the plate member 12.

Figure 11:
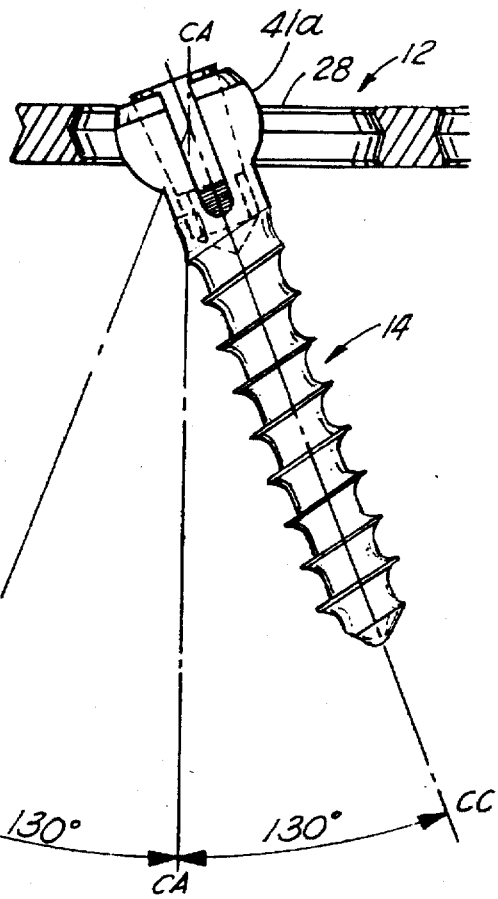
FIG. 11 is a fragmentary sectional view of an embodiment of the apparatus of the present invention illustrating a longitudinal range of angulation of an implanted bone screw.
Figure 12:
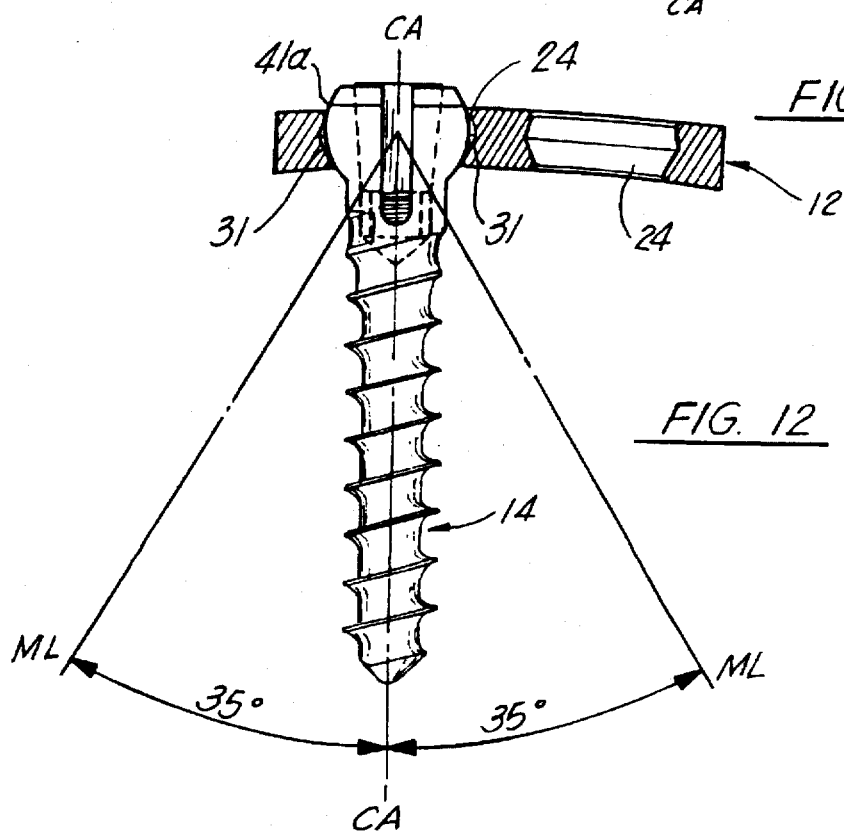
FIG. 12 is a fragmentary sectional view of an embodiment of the apparatus of the present invention illustrating a transverse range of angulation of an implanted bone screw.

The openings 24, 26 and the elongated slots 28 of the plate member 12 each form a cavity 30 with angled walls 31 extending between the upper and lower plate member surfaces 16, 18. The angled walls 31 form two inverted cones 31a, 31b with matching base circles 31c. The cavities 30 have smaller diameter wall portions 32 at the upper and lower plate surfaces 16, 18 and a central larger diameter wall portion 34 therebetween. The diameter of the wall portions 32 are larger at the upper surface 16 than the diameter of the wall portions 32 at the lower plate surface 18, but the diameter of the wall portions 34 is always larger than that at both the upper and lower surfaces 16, 18. The slightly smaller diameter of the wall portions 32 at the lower surface 18 of the plate member 12 keeps the bone screw 14 from slipping through the cavities 30 prior to insertion of the locking member 48 into the central bore 42 of the bone screw 14. The angulation of the wall surfaces 31 or the inverted cones 31a, 31b, between the upper and lower plate surfaces 16, 18, is generally about between 110° to 160°. The cavities 30 of the openings 24, 26 and slots 28 are shaped to allow for a transverse angulation of each of the bone screws 14 generally up to about 35° in both directions from the central vertical axis CA of the openings 24, 26 and slots 28 when each of the bone screws 14 is inserted into the openings 24, 26 and slots 28 (FIG. 12). The cavities 30 of the openings 24, 26 are shaped to allow for a longitudinal angulation of each of the bone screws 14 generally up to about 35° in both directions from the central vertical axis of the openings 24, 26 when each of the bone screws 14 is inserted into each of the openings 24, 26 (FIG. 12). The cavities 30 of the slots 28 are shaped to allow for a longitudinal angulation of each of the bone screws 14 of generally between 0° to 130° in both directions from the central vertical axis of the slots 28 when each of the bone screws 14 is inserted into each of the slots 28 (FIG. 11). The openings 24, 26 and slots 28 have a beveled surface 15 on the upper and lower plate surfaces 16, 18 as illustrated in FIGS. 4–6.

The geometry of the plate member 12, plus the load factors of the openings 24, 26 and slots 28, allow the plate member 12 to be somewhat bendable during implantation while still maintaining the rigidity needed for adequate fixation and immobilization of the vertebrae. Additionally, the ability of plate member 12 to have either a transverse or longitudinal curve allows for a closer fit to the contours of the vertebrae.

Figure 13:
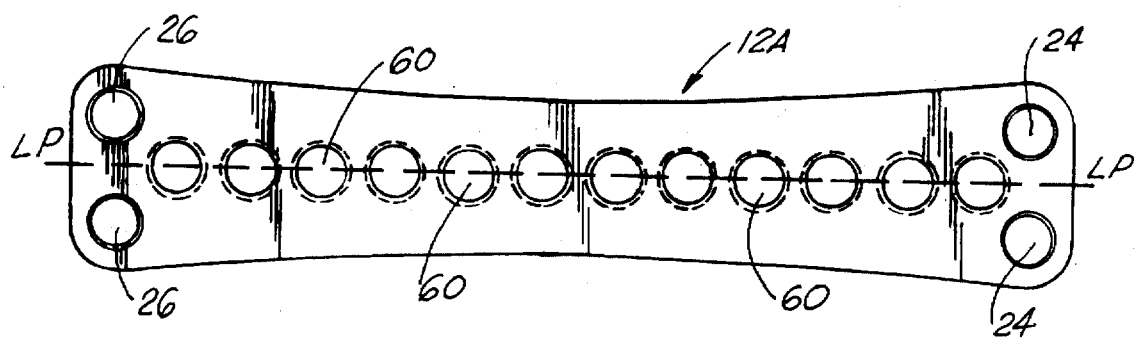
FIG. 13 is a plan view of another embodiment of the apparatus of the present invention illustrating a plate member.

FIG. 13 illustrates plate member 12A, an alternate embodiment of plate member 12, having a plurality of openings 60 positioned along the longitudinal plane LP of the plate member 12A. Each circular opening 60 is spaced at least about 1.8 to 2.0 millimeters apart from each other. The plurality of openings 60 can include any number of individual openings and in a preferred embodiment up to about sixteen (16) individual openings 60. Each of the plurality of openings 60 has the same configuration as the openings 24, 26. All other aspects of plate member 12A are the same as plate member 12.

Figure 14:
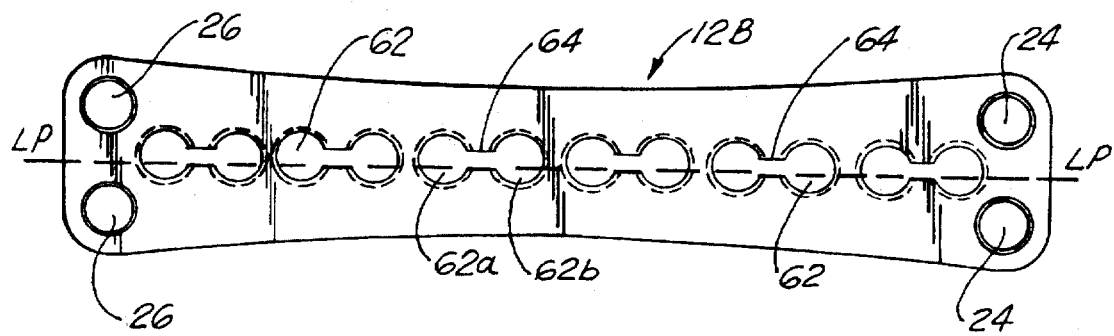
FIG. 14 is a plan view of another embodiment of the apparatus of the present invention illustrating a plate member.
Figure 15:
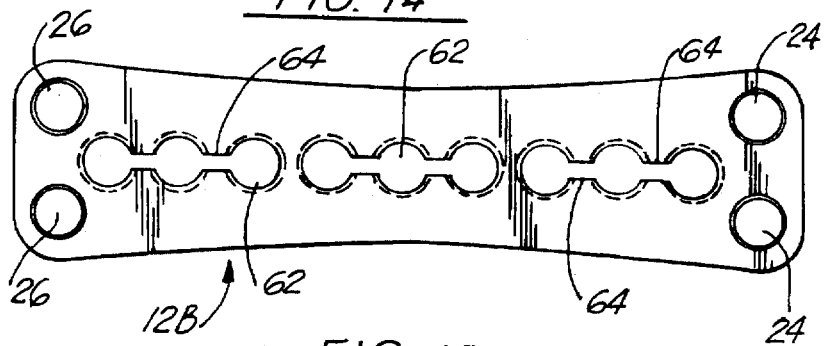
FIG. 15 is a plan view of an alternate configuration of the openings of the plate member of FIG. 14.
Figure 16:
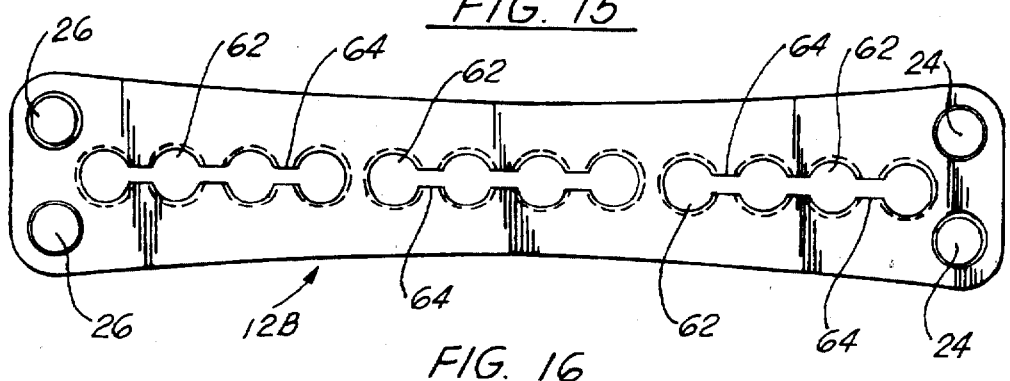
FIG. 16 is a plan view of an alternate configuration of the openings of the plate member of FIG. 14.

FIGS. 14–16 illustrates another alternate embodiment plate member 12, plate member 12B, which has a plurality of circular openings 62 positioned along the longitudinal plane LP of the plate member 12B with each circular opening 62a being connected to a next circular opening 62b by a narrow slot 64. The narrow slot 64 has a width that is equal to about between ⅓ to ½ the diameter of each circular opening 62 and a length that is between about 1.4 to 2.00 millimeters. The width of the narrow slot 64 is smaller than the diameter of any bone screw that would be inserted into the circular openings 62 and does not allow for the sliding of a bone screw between the circular openings 62a and 62b. The narrow slots 64 allow for controlled flexing of the plate member 12B. The connected circular openings 62 can be in groupings of two circular openings, three circular openings or four circular openings as illustrated in FIGS. 14–16. The groupings of circular openings 62 on the plate member 12B can be in any combination of the groupings of two, three or four circular openings 62. An example of the various combinations on plate member 12B is illustrated in FIGS. 14–16. Each of groupings of circular openings 62 are no less than 1.5 millimeters apart from the next grouping of circular openings 62. Each of the plurality of openings 62 has the same configuration as the openings 24, 26. All other aspects of plate member 12B are the same as plate member 12.

Figure 10:
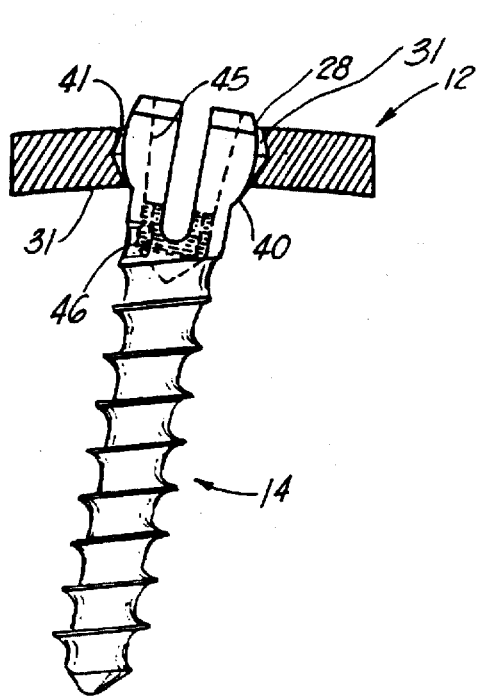
FIG. 10 is a fragmentary sectional view of an embodiment of the apparatus of the present invention illustrating the bone screw of FIG. 7 placed in an angled position.

The bone screw 14 (FIG. 7) has an elongated shank 36, a lower tip 37, and an enlarged upper portion 40 affixed to one end of the shank 36. The lower tip 37 of the bone screw 14 communicates with a helical thread 38 that begins at the lower tip 37 and terminates at the upper portion 40. The enlarged upper portion 40 has a generally ellipsoid-shaped outer surface 41, a generally cylindrical central bore 42 and upper walls 43. The upper walls 43 of the enlarged portion 40 have at least 2 radial slits 44 intersecting the bore 42, and in a preferred embodiment, four radial slits 44 intersecting the bore 42, as seen in FIG. 9. The central bore 42 includes internal threading 46 on a portion of the cylindrical surface 45, as illustrated in FIGS. 7 and 10. The ellipsoid-shaped surface 41 of the upper portion 40 interfaces with the cavities 30 of the openings 24, 26 and elongated slots (see FIG. 10) or the plurality of circular openings 60, 62, as will be described more fully hereinafter.

A locking member 48, as shown in FIG. 8, has lower and upper portions 50, 52 respectively and a top surface 51, with the locking member 48 being sized and shaped to fit into the cylindrical central bore 42 of the bone screw 14. The locking member 48 includes external threading 54 on its lower portion 50 which engages the corresponding internal threading 46 of the central bore 42. A tool receptive socket such as hexagonal socket 56 (FIG. 9) is provided on the flat top surface 51, so that the locking member 48 can be rotated using a hexagonal wrench or other such tool or instrument. When locking member 48 is threaded into the central bore 42 of bone screw 14, the upper walls 43 expand outwardly further enlarging the upper portion 40.

As shown in FIGS. 10–12, the angular shape of the cavity walls 31 allows for both transverse and longitudinal angulation of an implanted bone screw 14. The ellipsoid-shaped surface 41 allows the upper portion 40 of the bone screw 14 to be freely rotatable within the plate member cavity 30 prior to insertion of the locking member 48. After the bone screws 14 have been positioned within the openings 24, 26, slots 28 or plurality of circular openings 60, 62 of the plate members 12, 12A or 12B and implanted in the vertebrae of a patient, the locking members 48 are threaded into the central bore 42 of the bone screws 14. The threading 54 of the locking member 48 engages the threading 46 of the central bore 42 and the radial slits 44 allow the upper wall portions 43 to expand outwardly as the locking member 48 is tightened into the central bore 42 (FIG. 9).

When the locking member 48 is threaded into the central bore 42 of bone screw 14, the ellipsoid-shaped outer surface 41 of the upper portion 40 expands to a spherically-shaped outer surface 41a which causes the upper wall portions 43 to grip the cavity walls 31 so as to lock each bone screw 14 into a selected position within the openings 24, 26, slots 28 or plurality of circular openings 60, 62 of the plate members 12, 12A or 12B as illustrated in FIGS. 11 and 12. The geometry of the final expanded shape of the spherically-shaped outer surface 14 allows for an interference fit that provides a solid rigid mating mechanism within the conically-shaped cavities 30. The two inverted cones 31a, 31b with the matching base circles 31c of the cavities 30 provide for line contact with the spherically-shaped expanded outer surface 41 of the upper walls 43. This allows for a secure locking mechanism between the bone screw 14 and the plate member 12. This is particularly true because a spherically-shaped bone screw will deform into an ellipsoid-shape when expanded which will not engage in line contact with a spherically or conically shaped opening. The inventive locking mechanism between the plate member 12, 12A or 12B and the bone screws 14 locks the bone screws 14 into the plate member 12, 12A or 12B which prevents the implanted bone screws 14 from backing out of the plate member 12, 12A or 12B. This in turn prevents the bone screws 14 from backing out of the vertebrae. The ability of the inventive bone fixation apparatus 10 to lock the bone screws 14 into the plate member 12, 12A or 12B is critical in anterior cervical spine applications because if implanted bone screws back out of the vertebrae in this area of the spine the bone screws can cause serious injury to the patient. The present locking mechanism, plus the geometry of the plate member 12, 12A and 12B allows the bone fixation apparatus 10 to provide a rigid construct when initially implanted. However, as the implanted bone screws loosen over time, the bone fixation apparatus 10 becomes semi-rigid and provides a construct that is somewhat flexible and compliant. Further, the locking mechanism and the plate geometry allows for variable initial rigidity at the bone screw 14 and plate member 12, 12A and 12B interface. Variable rigidity of the locking mechanism means that the bone screw 14 can be locked into the plate member 12, 12A or 12B so as to provide a very rigid interface between the bone screw and the plate member in which there is no movement of the bone screw 14 within the cavity 30 or the bone screw 14 can be locked into the plate member 12, 12A or 12B so as to provide a less rigid interface between the bone screw and the plate member in which there is a small amount of movement or flexing of the bone screw 14 within the cavity 30.

During implantation, the configuration of the openings 24, 26 provides secure fixation at the ends of the plate member 12, 12A and 12B while the slots 28 and plurality of circular openings 60, 62 provide for a variation in screw placement along the longitudinal axis of the plate member 12, 12A and 12B. The bone fixation apparatus 10 can be sized to be used on cervical or lumbar vertebrae in either an anterior or posterior location. The bone fixation apparatus 10 can also be sized to be used on other bone surfaces in addition to vertebrae.

Although the present invention has been described with reference to its preferred embodiments, those skilled in the art will recognize changes which may be made in form or structure which do not part from the spirit of the invention already described in the specification and embodied in the claims which follow.

What is claimed is:

1. A bone fixation apparatus, comprising:
   a) an elongated plate member having a longitudinal plane, a longitudinal axis, upper and lower surfaces, apposed longitudinal side edges, at least two pairs of first circular openings and a series of second openings positioned along the longitudinal plane of the plate member, said first circular openings and said series of second openings each having a central vertical axis;
   b) said first circular openings and said series of second openings each forming a cavity with walls extending between the upper and lower plate member surfaces with at least a plurality of said cavities having smaller diameter portions at the plate member upper and lower surfaces and a larger diameter portion therebetween, said cavities being configured in the shape of two inverted cones with matching base circles for allowing transverse and longitudinal angulation of an implanted bone screw;
   c) a plurality of bone screws each having a threaded first end portion adapted for implantation into a patient's bone mass and an ellipsoid shaped enlarged second end portion;
   d) a locking member that connects to the second end portion of each bone screw for expanding the second end portion so as to grip the cavity wall of the plate member and for locking each bone screw into a selected position within the said first circular openings and said series of second openings of the plate member;

e) wherein the series of second opening includes a plurality of second openings having a diameter and positioned along the longitudinal plane of the plate with each second opening being connected to a next second opening by a narrow slot having a width not greater than ½ the diameter of the second opening which allows for controlled flexing of the plate.

2. The apparatus of claim 1, wherein the second end portion of each bone screw has a cylindrical central bore and at least two radial slits intersecting the bore, said central bore including threading on a portion of a surface of the bore.

3. The apparatus of claim 2, wherein each bone screw has four radial slits intersecting the bore.

4. The apparatus of claim 2, wherein the locking member is sized and shaped to fit into the central bore of each bone screw and has threading on a portion of a surface of the locking member for engaging the threading on the surface of the bore.

5. The apparatus of claim 1, wherein said plate member has a transverse plane and is formed so as to include a curve in the transverse plane.

6. The apparatus of claim 1, wherein said plate member is formed so as to include a curve in the longitudinal plane of the plate member.

7. The apparatus of claim 1, wherein the plate member has a first end, a second end and a center portion with the apposed longitudinal side edges having a smaller width at the center portion in relation to a larger width at the first and second ends.

8. The apparatus of claim 7, wherein one pair of first circular openings is positioned at the first end of the plate and the second pair of first circular openings is positioned at the second end of the plate.

9. The apparatus of claim 1, wherein the plurality of second openings includes circular openings with each of the plurality of second circular openings being spaced at least about 1.8 to 2.0 millimeters apart from each other.

10. The apparatus of claim 9, wherein the plurality of second circular openings includes a series of at least two spaced apart second circular openings.

11. The apparatus of claim 9, wherein the plurality of second circular openings includes a grouping of two second circular openings being connected to each other by the narrow slot.

12. The apparatus of claim 9, wherein the plurality of second circular openings includes a grouping of three second circular openings, each second circular opening being connected to the next second circular opening by the narrow slot.

13. The apparatus of claim 9, wherein the plurality of second circular openings includes a grouping of four second circular openings, each second circular opening being connected to the next second circular opening by the narrow slot.

14. The apparatus of claim 9, wherein the series of second openings includes any combination from the group consisting of two second circular openings being connected to each other by the narrow slot; three second circular openings, each second circular opening being connected to the next second circular opening by the narrow slot; and four second circular openings, each second circular opening being connected to the next second circular opening by the narrow slot.

15. The apparatus of claim 1, wherein the first circular openings and series of second openings allow for transverse angulation of each of the bone screws of up to about 35° in each direction from the central vertical axis of the first circular openings and the series of second openings when each of the bone screws is inserted into each of the first circular openings and each of the series of second openings.

16. The apparatus of claim 1, wherein the first circular openings and series of second openings allow for longitudinal angulation of each of the bone screws of up to about 35° in each direction from the central vertical axis of the first circular openings and the series of second openings when each of the bone screws is inserted into each of the first circular openings and each of the series of second openings.

17. The apparatus of claim 1, wherein the first circular openings and series of second openings include a beveled surface on the upper and lower surfaces of the plate member.

18. The apparatus of claim 1, wherein the plate member is sized to be placed on adjoining cervical vertebrae.

19. The apparatus of claim 1, wherein the plate member is sized to be placed on adjoining lumbar vertebrae.

20. The apparatus of claim 1, wherein the plate member is sized to be placed on an anterior side of the cervical vertebrae.

21. A bone fixation apparatus, comprising:

a) an elongated plate member having a longitudinal plane, a longitudinal axis, upper and lower surfaces, apposed longitudinal side edges, at least two pairs of first circular openings and a series of second openings positioned along the longitudinal plane of the plate member, said first circular openings and said series of second openings each having a central vertical axis;

b) said first circular openings and said series of second openings each forming a cavity with walls extending between the upper and lower plate member surfaces with at least a plurality of said cavities having smaller diameter portions at the plate member upper and lower surfaces and a larger diameter portion therebetween, said cavities being configured in the shape of two inverted cones with matching base circles for allowing transverse and longitudinal angulation of an implanted bone screw;

c) a plurality of bone screws each having a threaded first end portion adapted for implantation into a patient's bone mass and an ellipsoid shaped enlarged second end portion;

d) a locking member that connects to the second end portion of each bone screw for expanding the second end portion so as to form an interference fit between the second end portion of each bone screw and the cavity wall of a selected first circular opening or selected series of second openings of the plate member which allows each bone screw to be locked into a selected position within the said first circular opening and said series of second openings of the plate member;

e) wherein the series of second opening includes a plurality of second openings having a diameter and, positioned along the longitudinal plane of the plate with each second opening being connected to a next second opening by a narrow slot having a width not greater than ½ the diameter of the second opening which allows for controlled flexing of the plate.

22. The apparatus of claim 21, wherein the interference fit between the expanded second end portion of each bone screw and the cavity wall of the selected first circular opening or selected series of second openings of the plate member create a locking mechanism that allows for variable rigidity of the locking mechanism at each bone screw and plate member interface.

23. A bone fixation apparatus, comprising:

a) an elongated plate member having a longitudinal plane, a longitudinal axis, upper and lower surfaces, apposed longitudinal side edges, at least two pairs of first circular openings and a series of second openings positioned along the longitudinal plane of the plate member, said first circular openings and said series of second openings each having a central vertical axis;

b) said first circular openings and said series of second openings each forming a cavity with walls extending between the upper and lower plate member surfaces with at least a plurality of said cavities having smaller diameter portions at the plate member upper and lower surfaces and a larger diameter portion therebetween, said cavities being configured in the shape of two inverted cones with matching base circles for allowing transverse and longitudinal angulation of an implanted bone screw;

c) said plate member having a first end, a second end and a center portion with the apposed longitudinal side edges having a smaller width at the center portion in relation to a larger width at the first and second ends;

d) said one pair of first circular openings being positioned at the first end of the plate member and the second pair of first circular openings being positioned at the second end of the plate member;

e) wherein the series of second openings includes a plurality of second openings having a diameter and positioned along the longitudinal plane of the plate with each second opening being connected to a next second opening by a narrow slot having a width not greater than ½ the diameter of the second opening which allows for controlled flexing of the plate.

24. The apparatus of claim 23, wherein said plate member has a transverse plane and is formed so as to include a curve in the transverse plane.

25. The apparatus of claim 23, wherein said plate member is formed so as to include a curve in the longitudinal plane of the plate member.

26. The apparatus of claim 23, wherein the plurality of second openings includes circular openings with each of the plurality of second circular openings being spaced at least about 1.8 to 2.0 millimeters apart from each other.

27. The apparatus of claim 26, wherein the plurality of second circular openings includes a series of at least four spaced apart second circular openings.

28. The apparatus of claim 26, wherein the plurality of second circular openings includes a grouping of two second circular openings being connected to each other by the narrow slot.

29. The apparatus of claim 26, wherein the plurality of second circular openings includes a grouping of three second circular openings, each second circular opening being connected to the next second circular opening by the narrow slot.

30. The apparatus of claim 26, wherein the plurality of second circular openings includes a grouping of four second circular openings, each second circular opening being connected to the next second circular opening by the narrow slot.

31. The apparatus of claim 26, wherein the series of second openings includes any combination from the group consisting of two second circular openings being connected to each other by the narrow slot; three second circular openings, each second circular opening being connected to the next second circular opening by the narrow slot, and four second circular openings, each second circular opening being connected to the next second circular opening by the narrow slot.

32. The apparatus of claim 23, wherein the first circular openings and series of second openings allow for transverse angulation of each of the bone screws of up to about 35° in each direction from the central vertical axis of the first circular openings and the series of second openings when each of the bone screws is inserted into each of the first circular openings and each of the series of second openings.

33. The apparatus of claim 23, wherein the first circular openings and series of second openings allow for longitudinal angulation of each of the bone screws of up to about 35° in each direction from the central vertical axis of the first circular opening and the series of second openings when each of the bone screws is inserted into each of the first circular openings and each of the series of second openings.

34. The apparatus of claim 23, wherein the first circular openings and series of second openings include a beveled surface on the upper and lower surfaces of the plate member.

35. The apparatus of claim 23, wherein the plate member is sized to be placed on adjoining cervical vertebrae.

36. The apparatus of claim 23, wherein the plate member is sized to be placed on adjoining lumbar vertebrae.

37. The apparatus of claim 23, wherein the plate member is sized to be placed on an anterior side of the cervical vertebrae.

* * * * *